United States Patent [19]
Matern

[11] Patent Number: 5,725,539
[45] Date of Patent: Mar. 10, 1998

[54] SURGICAL INSTRUMENT USED TO CLAMP A VESSEL OR THE LIKE

[75] Inventor: Ulrich Matern, Bollschweil, Germany

[73] Assignee: Klinikum Der Albert-Ludwigs-Universität Freiburg, Freiburg, Germany

[21] Appl. No.: 647,904
[22] PCT Filed: Nov. 26, 1994
[86] PCT No.: PCT/EP94/03916
 § 371 Date: May 30, 1996
 § 102(e) Date: May 30, 1996
[87] PCT Pub. No.: WO95/15121
 PCT Pub. Date: Jun. 8, 1995

[30] Foreign Application Priority Data
 Dec. 1, 1993 [DE] Germany .................. 43 40 821.4

[51] Int. Cl.⁶ ............................................... A61B 17/08
[52] U.S. Cl. ......................................... 606/151; 606/148
[58] Field of Search .............................. 606/151, 148, 606/228, 144, 139

[56] References Cited

U.S. PATENT DOCUMENTS

| | | |
|---|---|---|
| 5,207,694 | 5/1993 | Broomé . |
| 5,336,231 | 8/1994 | Adair .............................. 606/148 |
| 5,454,820 | 10/1995 | Kammerer et al. .............. 606/148 |
| 5,569,274 | 10/1996 | Rapacki et al. .................. 606/151 |

FOREIGN PATENT DOCUMENTS

| | | |
|---|---|---|
| A-3504202 | 8/1985 | Germany . |
| C-4228910 | 6/1993 | Germany . |
| WO-A-9006725 | 6/1990 | WIPO . |

*Primary Examiner*—Michael Buiz
*Assistant Examiner*—Kevin Truong
*Attorney, Agent, or Firm*—Panitch Schwarze Jacobs & Nadel, P.C.

[57] ABSTRACT

A surgical instrument (1) is used to clamp a vessel (6), hollow organ or the like. The instrument has essentially a lock assembly (3) with a thread holder (4) and a shaft-like lock assembly holder (5) that can be coupled to the lock assembly. The lock assembly holder can be coupled with the lock assembly and has actuating members (7) for opening and closing the lock assembly thread holder. One thread end (12) is connected to the lock assembly (3) and with the aid of forceps (25) extended through the instrument can be grasped and drawn through two clamping jaws (9) spring-loaded towards each other. A loop is formed around the vessel (6) and the thread drawn to clamp off this vessel. After lock assembly (3) and lock assembly holder (5) have been detached from each other, the drawn-through thread end is clamped and the lock assembly holder (5) as well as the forceps (25) can then be removed. The thread (2) can be varied in tension as required and can be released again by opening the clamping device, preferably using the lock assembly holder (5).

16 Claims, 6 Drawing Sheets

SURGICAL INSTRUMENT USED TO CLAMP A VESSEL OR THE LIKE

FIELD OF THE INVENTION

The invention relates to a surgical instrument used to clamp (ligature) a vessel, hollow organ or similar part of the body by means of a thread or rein, particularly in minimum invasive surgery.

BACKGROUND OF THE INVENTION

When applying a ligature, i.e. tying off vessels and the like, a so-called rein in the form of a thread, a plastic hose or a rubber thread is used for wrapping round the vessel. This rein is looped around the vessel to be ligated and then knotted.

There is furthermore the possibility of using haemostatic forceps for ligating, but they can be used only for a short period as they are in the way in the operating area.

While a ligature is comparatively simple to apply if the abdomen is open, considerable problems arise if the abdomen is closed and instruments are introduced by way of trocar sleeves, because the room for movement is very restricted.

As a result, it is very time-consuming to apply the ligature. A further drawback is that the tension of the ligature can no longer be altered after knotting.

A ligature system usable in conjunction with trocars is known from WO 90/06725. It has a thread which can be drawn with its end into a cavity and can be fixed there by retaining means, particularly by locking profiles. For drawing in the end of the thread, a pulling element is provided which can be fed through the trocar sleeve. Using the pulling element, the thread end can be grasped and the loop can be drawn tight. Slackening of the ligature is not possible in this instance either.

When ligating a blood vessel or the like, it is therefore not possible by slackening the ligature to check whether, for example, a suture is tight. Hence neither is temporary blood circulation or temporary perfusion of an organ possible in a simple manner. Therefore such cases necessitate that in a complicated way the first ligature be severed and then if necessary a new ligature be applied again.

SUMMARY OF THE INVENTION

The object underlying the present invention is to provide an auxiliary surgical instrument of the kind mentioned at the outset, with the aid of which a ligature can be applied in a significantly simpler fashion and in a short space of time. This is to be possible particularly also in minimum invasive surgery and when operating through trocar sleeves or the like. In addition, it is possible for the ligature to be temporarily loosened and then tightened again.

To accomplish this object it is proposed according to the invention particularly that the instrument has a lock assembly with a thread holder and a shaft-like lock assembly holder that can be coupled with the lock assembly, and that the lock assembly holder has actuating members for opening and closing the lock assembly thread holder.

Using this instrument, a ligature can be carded out in a simple manner by putting the lock assembly with the aid of the lock assembly holder at the vessel to be ligated and by the lock assembly there clampingly holding the thread looped round the vessel. The lock assembly holder can then be removed so as not to be in the way in the operating area.

By the same token, the lock assembly holder can also be coupled with the lock assembly again for removing or loosening the ligature. Using this instrument, the ligature can also be applied as well as possibly removed particularly quickly; a factor of especial significance for a number of operations. It is furthermore advantageous that the handling is possible without any difficulty, even in very confined conditions.

Suitably, the actuating members of the lock assembly holder at the same time compose coupling elements for connecting to the lock assembly. This contributes towards simple handling of the instrument. If the lock assembly holder is coupled with the lock assembly, the thread holder is simultaneously held in the open position. During uncoupling, the thread holder automatically assumes the clamping position and then holds the intermediate end of the rein fast. Additional actuation for clamping or releasing the end of the rein is not necessary in this embodiment.

According to a further development of the invention it is proposed that the thread holder of the lock assembly has clamping elements for holding at least one loop end of the rein or thread, and that preferably one thread end is fixed at the lock assembly and the other thread end is held by the clamping elements. Thus the free thread end is first conducted around the vessel or the like to be clamped and is then held fast by the clamping elements after lock assembly and lock assembly holder have been detached from each other.

It is especially advantageous if the clamping elements are configured and arranged to be self-locking counter to the tensioning direction of the thread and if the clamping elements have clamping jaws spring-loaded in the clamping direction which are mounted for swivelling towards each other and can be acted upon in the clamping direction by the tension of the thread.

As a result of this configuration of the clamping means and thread holder, the thread can still be retightened and tautened even after the lock assembly holder has been uncoupled and thus the thread tension can be adjusted particularly well to the respective requirements.

The lock assembly preferably has a passage, particularly a central passage, for one thread end. The free thread end can be drawn through this passage to form a loop.

The lock assembly holder, particularly its shaft, suitably has a preferably central passage in alignment with that of the lock assembly in the coupled position of lock assembly and lock assembly holder, and forceps are provided which fit through these passages and can be inserted from the outer end of the lock assembly holder.

Using the forceps or the like extended through the lock assembly holder and lock assembly, the free thread end looped around the vessel to be clamped can be grasped and passed through the clamping device. After the lock assembly holder has been uncoupled, the loop width can be appropriately adjusted by pulling the thread end.

One embodiment of the invention envisages that the lock assembly holder has actuating and holding elements in the form of forcipated clasping jaws preferably having their inner surfaces adapted generally to the outer contour of the lock assembly and in the closed position engaging the actuating projections to unclamp the thread. By this means, the lock assembly holder has a comparatively small outer cross section and thus can also be introduced well through trocar sleeves for example.

Another embodiment of the invention contemplates that the clamping elements of the thread holder take the form of expanding jaws and have a passage therebetween for the thread, that the expanding jaws are provided with an external clamping cone co-operating with a slidable clamping sleeve, that the clamping sleeve is spring-loaded in the closing direction and that the clamping elements and the clamping cone are provided with contact points for the lock assembly holder or the like for opening and closing the clamping elements. The thread is clamped here by the clamping elements being externally acted upon with the aid of the slidable, spring-loaded clamping sleeve.

BRIEF DESCRIPTION OF THE DRAWINGS

Additional developments of the invention are recited in the further sub-claims. The invention with its leading features will be described in closer detail below with reference to the drawings in which

DETAILED DESCRIPTION OF PREFERRED EMBODIMENTS

Figure 1:
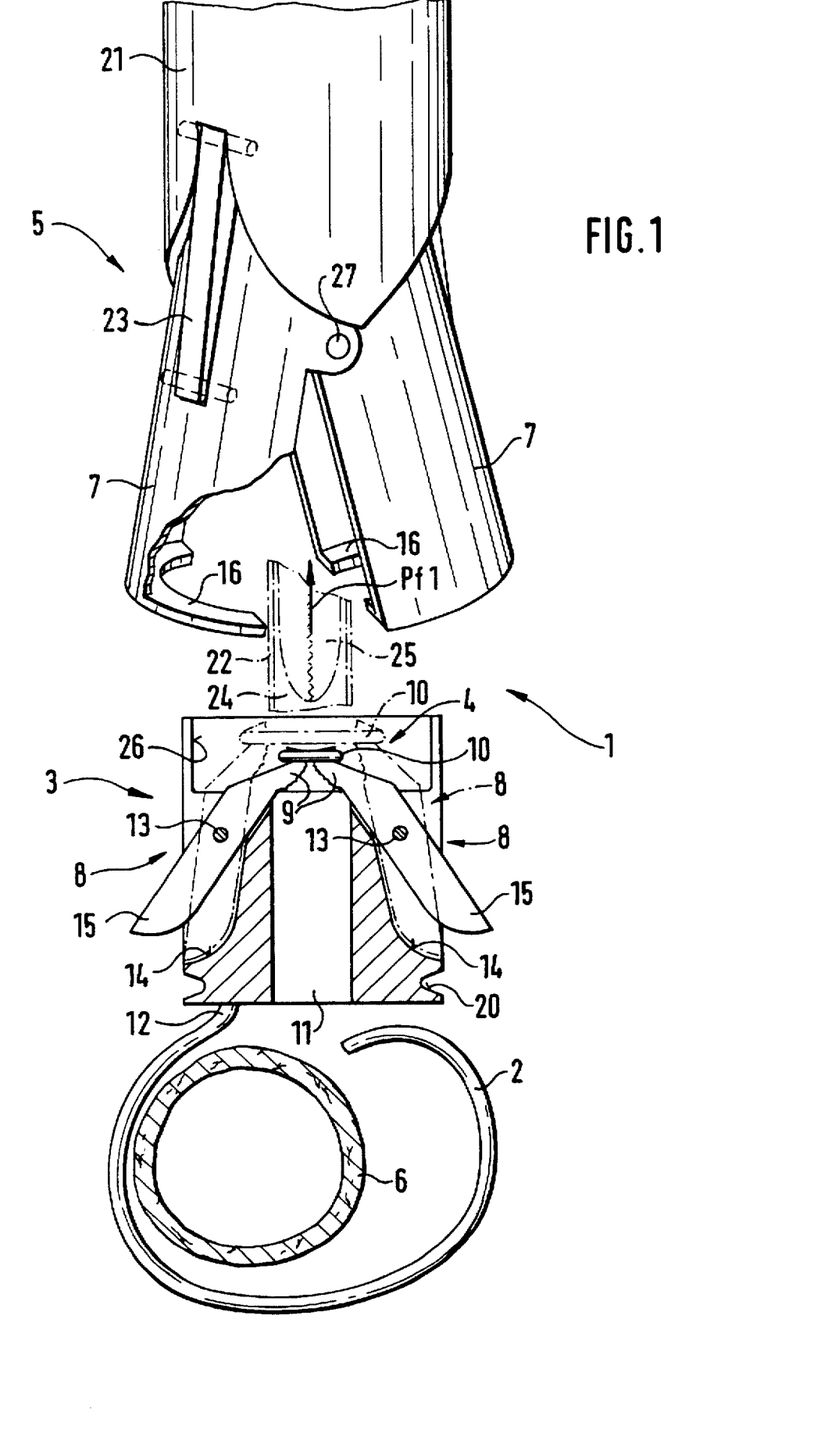
FIG. 1 is a side view of an instrument embodying the invention, with lock assembly and lock assembly holder in a position detached from each other.

A surgical instrument 1 (FIG. 1) serves to clamp a vessel or the like by means of a thread 2 (rein) and has essentially a lock assembly 3 with a thread holder 4 and a lock assembly holder 5 here shown only in part. To position the lock assembly 3 at a vessel 6 to be clamped, the lock assembly 3 can be coupled with the lock assembly holder 5. The lock assembly holder 5 has for this purpose clasping jaws 7 adapted to open and close in a gripper-like fashion. In FIG. 1 the clasping jaws 7 are illustrated in an open i.e. gripping position, so that the lock assembly holder 5 can be slipped with these clasping jaws over the lock assembly 3.

The clasping jaws 7 simultaneously form actuating members for opening and closing the lock assembly thread holder 4. In the exemplary embodiment shown, the thread holder 4 is in principle designed like a so-called curry haemostat. For this purpose clamping elements 8 are provided which take the form of pivoted levers and at their inner ends have spring-loaded clamping jaws 9. These clamping jaws 9 clamp an intermediate thread 2. As a result of the position and configuration of the clamping elements 8, the passed-through thread 2 is selflockingly held. Therefore on the one hand the thread 2 can be drawn through the clamping elements 8 in the tensioning direction according to arrow Pf 1, but on the other hand the clamping of the thread is automatically increased and thus the thread is securely held counter to this tensioning direction. A rubber ring 10 is applied to the clamping jawends of the clamping elements 8, so that in the unloaded position the clamping elements 8 assume the position depicted by continuous lines in FIG. 1.

Figure 3:
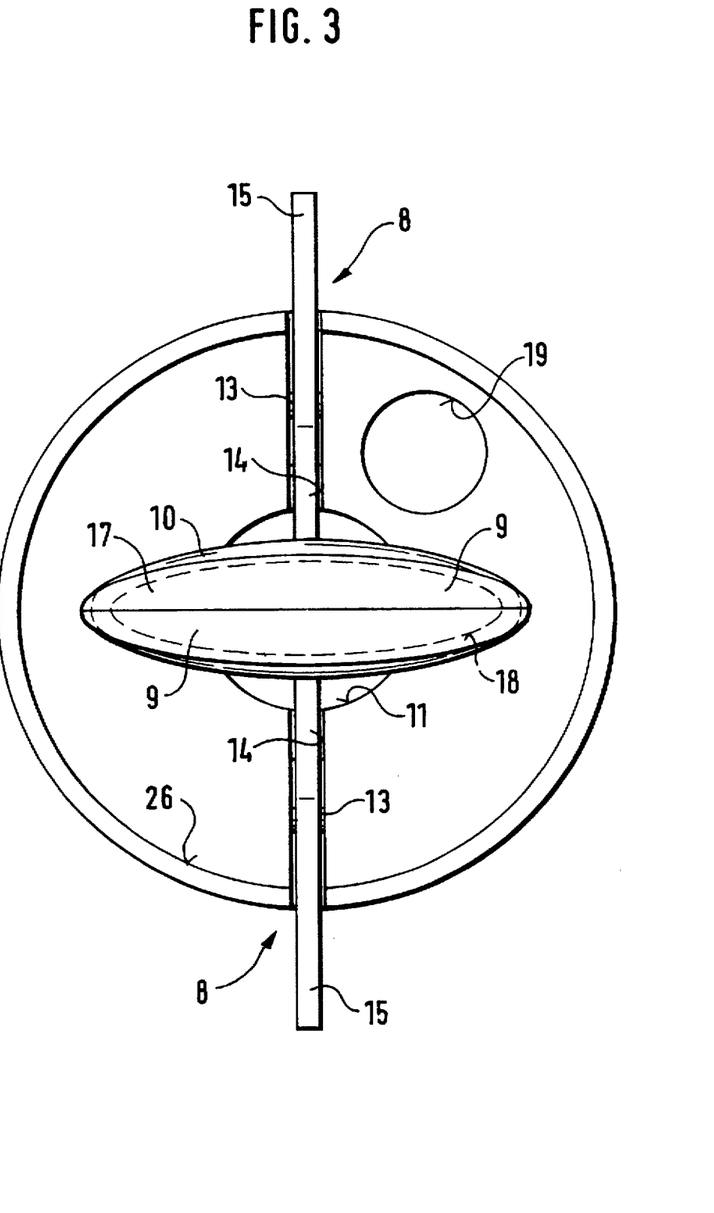
FIG. 3 is a view of the end face of the lock assembly shown in FIG. 2, with the thread holder closed.
Figure 4:
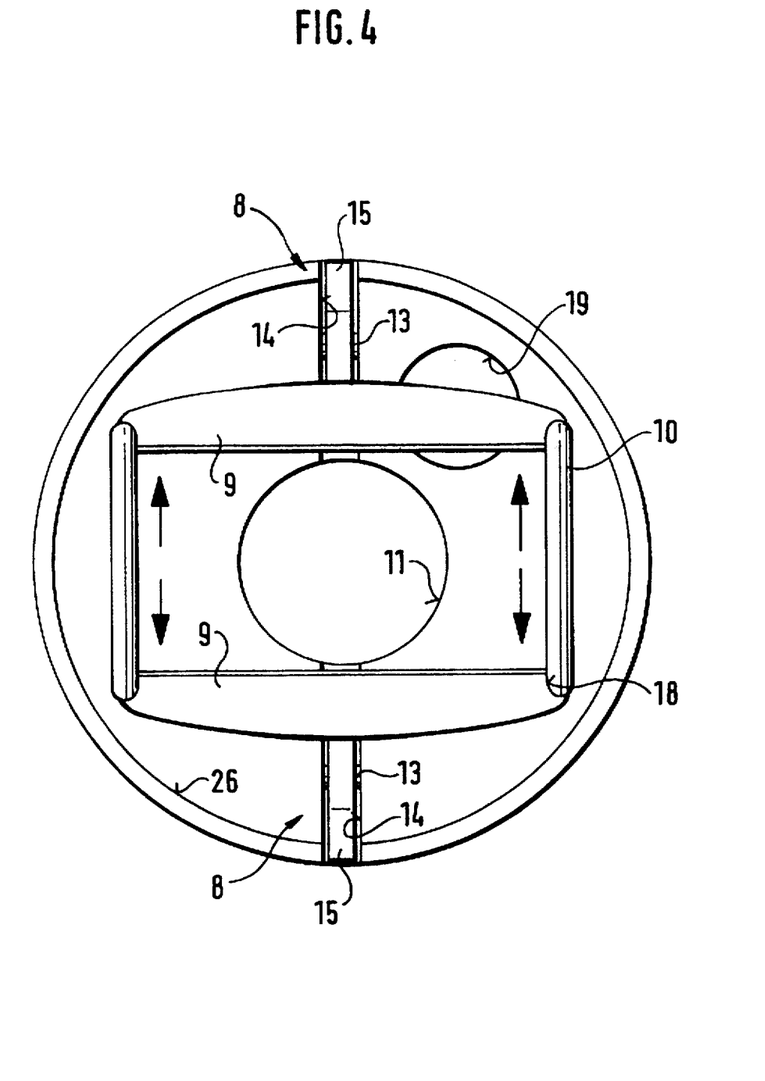
FIG. 4 is the end face of the lock assembly in a view corresponding substantially to FIG. 3, but with the thread holder open.

The lock assembly 3 has a central passage 11 through which the one thread end can be passed and then also extends between the clasping jaws 7 interfering with this passage 11 (cf. also FIGS. 3 and 4). The other thread end 12 is fixed to the lock assembly 3, so that a loop is formed when a free thread end is drawn through the lock assembly, or more specifically through its passage 11.

The clamping elements 8 resembling pivoted levers have swivel bearings 13 located in the wall of the lock assembly body and traversing slit-like pockets 14 for the clamping elements 8 in the lock assembly case.

The ends of the clamping elements facing away from the clamping jaws 9 have actuating projections 15 continuing beyond the swivel bearings 13. In the position of the clamping elements 8 depicted by continuous lines in FIGS. 1 and 2, the actuating projections 15 project beyond the outer periphery of the lock assembly 3 (cf. also FIG. 3).

Figure 5:
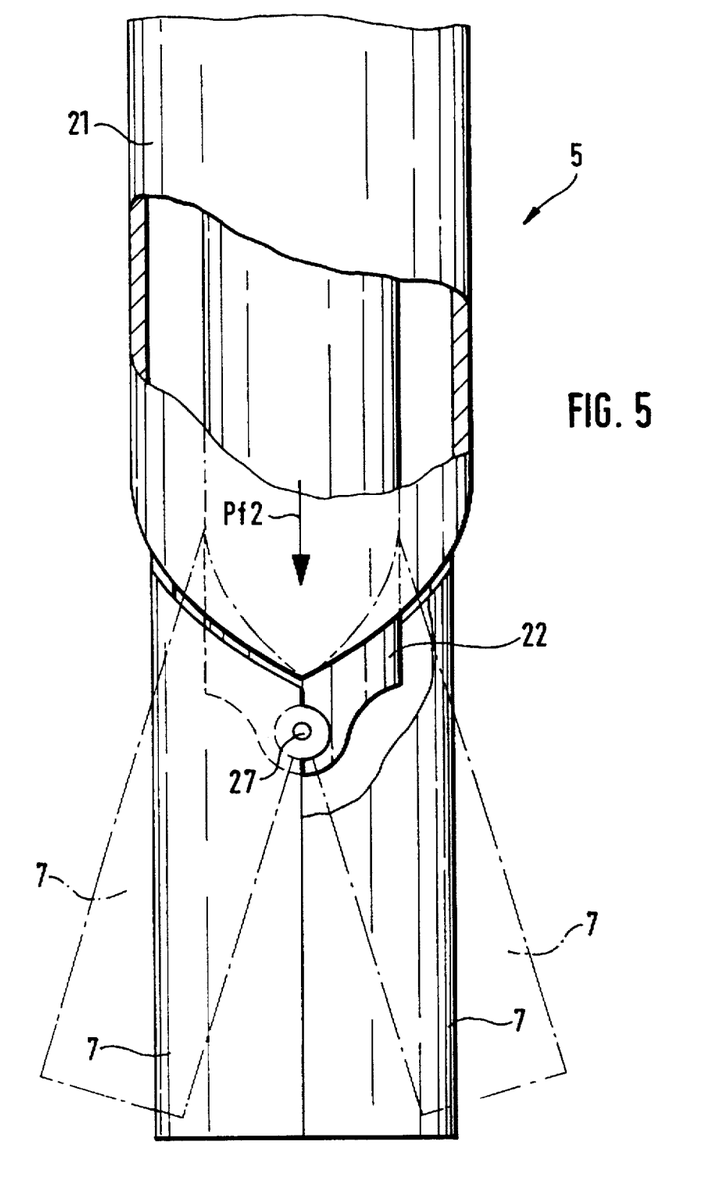
FIG. 5 is a side view of the inner end of the lock assembly holder and FIG. 6 is a view corresponding substantially to FIG. 5, but here with forceps extended through the lock assembly holder.

If now the lock assembly holder with its clasping jaws 7 is slipped over the lock assembly 3 and then the clasping jaws assume their closed position shown in FIG. 5, the actuating projections 15 of the clamping elements 8 are engaged and swivelled inwards into the pockets 14. At the same time the thread holder 4 is opened against the restoring force of the rubber ring 10. This position of the clamping elements 8 is depicted by dashed lines in FIGS. 1 and 2.

The free ends of the clasping jaws 7 have inwardly directed offsets 16 engaging with an annular groove 20 of the lock assembly 3 in the closed position of the clasping jaws 7. In this position, the lock assembly 3 and the lock assembly holder 5 are coupled together.

The passage 11 has a widening 26 in the region of the clamping jaws 9, so that there is sufficient room for the expansion of the clamping jaws 9 and also for the restoring element (rubber ring 10). As is evident from FIGS. 3 and 4, the clamping jaw-ends remote from the bearings are formed with tongues 17 composing grooved portions 18 for receiving the rubber ring 10.

FIGS. 3 and 4 show in addition to passage 11, a further passage 19. The thread end 12 to be secured can be passed through the passage 19 and also fixed there if necessary. In the simplest case, the thread end 12 is passed through the lock assembly 3, or more specifically through passage 19, from underneath and knotted at the other end.

The lock assembly holder 5 is shaft-like and is of a length adapted to the respective operating conditions. At the inner end are the actuating members in the form of clasping jaws 7 for engaging the actuating projections 15 of the clamping elements 8. These actuating members simultaneously form coupling elements for connecting to the lock assembly 3. For establishing the connection, the offsets 16 of the clasping jaws 7 engage with the annular groove 20 of the lock assembly 3. Handle-like actuating means (not shown) for opening and closing the clasping jaws 7 may be provided at the outer end of the lock assembly holder 5. The means for transferring this movement extend in the interior of the lock assembly holder 5. The lock assembly holder 5 has a tubular shaft member 21. Contained within this tubular shaft member 21 is a longitudinally slidable inner tube 22. This movement is effected from the outer end, by means of a corresponding handle element for instance.

As may be seen particularly in FIG. 5, the swivel bearings 27 of the clasping jaws 7 are provided at the inner end of this inner tube 20. This end of the inner tube 22 with the swivel beatings 27 is somewhat proud of the inner end of the shaft member 21 forming an outer tube.

Figure 6:
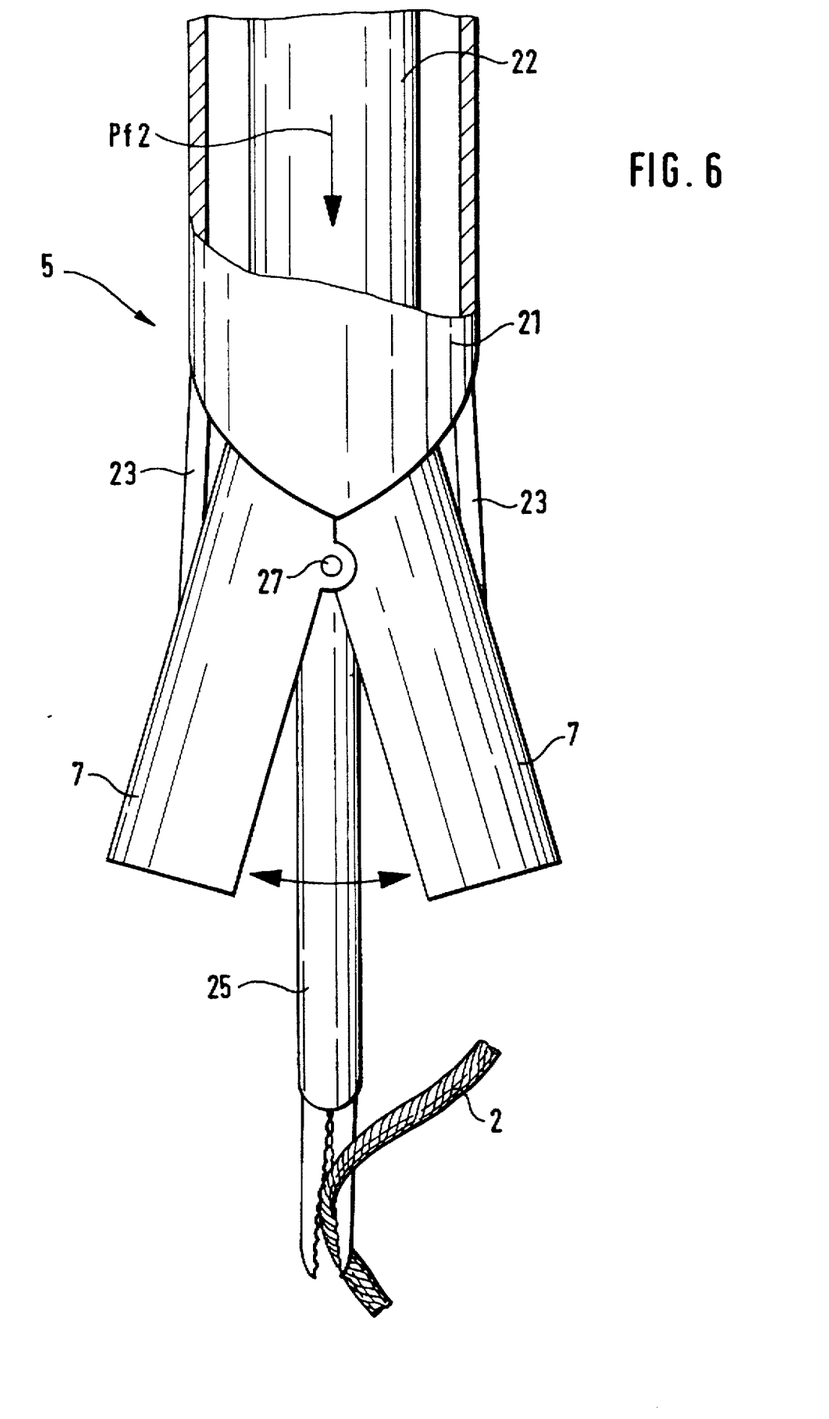

In the closed position (FIG. 5), the clasping jaws 7—as concerns their outer contour compose an extension of the shaft member 21 and are each formed by a channel-like tubing 10 section halved substantially lengthwise. The swivel bearings 27 are situated near the end of the shaft member 21 in the region of the centre longitudinal plane, so that the clasping jaws 7 are capable of swinging out in a gripper-like fashion as is indicated in FIG. 6 and by dashed lines in FIG. 5.

In order that this gripper movement takes place in synchronism by both clasping jaws 7 during a longitudinal movement of the inner tube 22, the clasping jaws 7 are in each case coupled with push-pull arms 23 (cf. FIG. 1) in laterally spaced relationship to the axis of the swivel bearings. The other ends of the push-pull arms are connected to the shaft member 21. By this means a positive control is constituted, bringing about an opening and closing swivel movement of the clasping jaws 7 as inner tube 22 moves relative to shaft member 21.

To swivel open the clasping jaws into a gripping position (FIG. 6), the inner tube 22 is moved slightly in the direction of arrow Pf 2, hence towards the inner end, so that the axis of the swivel bearings is also shifted further outwards. Since the clasping jaws are externally connected in the present instance by way of push-pull arms 23 flexibly coupled on the one hand to the clasping jaws 7 and on the other hand to the shaft member 21, the clasping jaws 7 are swivelled open into the gripping position at the same time as the swivel bearings 27 are displaced outwardly. Instead of the push-pull arms 23 provided, one might also provide pulling elements operative for the swivel-open movement and stops operative between the shaft member and the clasping jaws for the closing movement.

To apply a ligature, one proceeds as follows:

In the initial position, the lock assembly 3 is connected to the lock assembly holder 5 and held by the clasping jaws 7. The one end 12 of the thread 2 is connected to the lock assembly 3. The thus configured instrument is then brought, inner lock assembly end first, into the region of the vessel 6 to be ligated.

Figure 2:
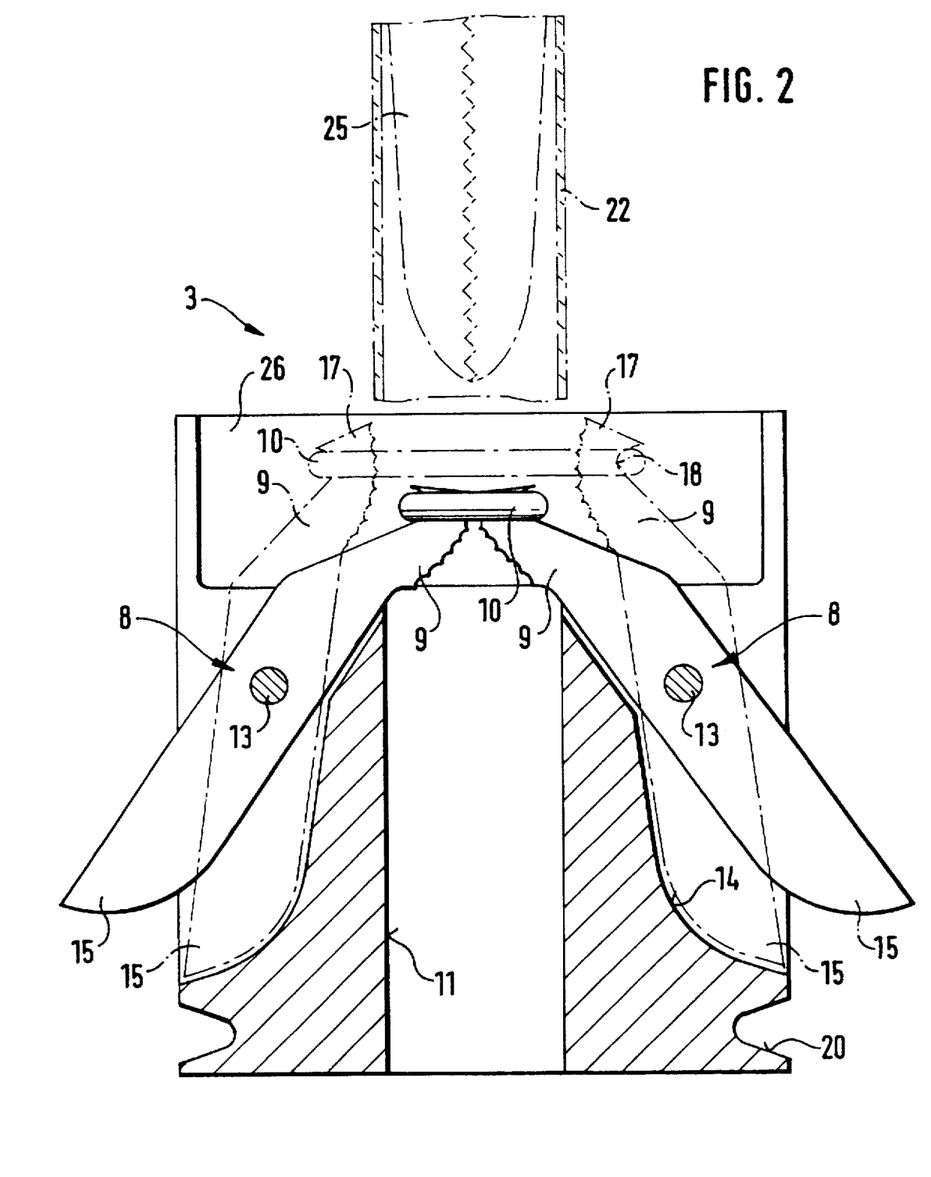
FIG. 2 is an enlarged view of the lock assembly shown in FIG. 1.

The inner tube 22 of the lock assembly holder 5 has throughout its length an inside cavity 24 indicated by dashed lines in FIGS. 1 and 2. Forceps 25 can now be passed through this inside cavity 24 and through the lock assembly passage 11 in alignment therewith in the coupled position of lock assembly holder and lock assembly (FIGS. 1, 2 and 6), and can grasp the free end of the thread 2 looped round the vessel 6. Since in this position the actuating projections 15 of the clamping elements 8 are engaged by the clasping jaws 7, the clamping jaws 9 are in the open position, as is indicated by dashed lines in FIGS. 1, 2 and 4. In this position the forceps 25 can thus be passed without hindrance through the instrument. The free thread end grasped by the passed-through forceps 25 is then drawn through the lock assembly 3. The lock assembly holder 5 can then be detached from the lock assembly 3 by opening the clasping jaws 7, whereby the clamping elements 8 automatically swivel into the clamping position and the drawn-through thread is clamped between the clamping jaws 9. Using the forceps 25, the thread 2 can be tautened in the direction of arrow Pf 1 and the tension adapted to the respective conditions.

By the same token, the special design of the thread holder 4 (curry haemostat) prevents any slackening of the thread tension because the clamping elements 8 act self-lockingly. Once the appropriate tension of the thread or rein has been set, only the lock assembly 3 remains in the region of the clamped vessel 6.

The tension of the rein can be slackened again in case of need. For that purpose the thread end drawn through the lock assembly 3 is grasped by the forceps extended through the lock assembly holder 5, as is shown in FIG. 6. The somewhat tautened thread can then serve as a guiding cord for the lock assembly holder 5 which is slid, along the forceps and the thread they hold, onto the lock assembly 3 quickly and without any difficulty. With the aid of the lock assembly holder 5 the clamping elements 8 are swivelled so that the thread 2 is released and can be slackened so far as to enable, for instance, the vessel 6 to be supplied with blood. In case of need, the rein can then be tightened again to clamp the vessel.

As already mentioned above, in the closed position (FIG. 5) the clasping jaws 7 compose an extension of the shaft member 21 and neither is there any cross-sectional enlargement in the region of these clasping jaws 7. Even when the lock assembly 3 is in the held and coupled condition, the instrument 1 as a whole forms a substantially smooth, slender tube length, so as also to lend itself especially well to use in operations through trocar sleeves.

I claim:

1. In combination, a surgical instrument (1) and a lock assembly (3) which is applied by the surgical instrument to clamp one of a vessel, a hollow organ and a body part using a thread, the combination comprising:

a lock assembly (3) having a thread holder (4) which is movable between an open position, in which a thread can be inserted or released, and a closed position, in which the thread is held firmly in position, such that a thread can be applied around the one of the vessel, hollow organ and body part and inserted in the thread holder when the thread holder is in the open position and be held when the thread holder is actuated to the closed position to act as a releasable clamp; and a surgical instrument (1) having a shaft with a lock assembly holder (5) located at a distal end thereof, the lock assembly holder including actuating members that are releasably coupled with the lock assembly (3) in a coupled position for positioning the lock assembly and moving the thread holder (4) between the open and closed positions to effectuate clamping.

2. The combination of claim 1 wherein the actuating members of the lock assembly holder (5) include coupling elements connected to the lock assembly (3).

3. The combination of claim 1 wherein the thread holder (4) of the lock assembly (3) includes clamping elements (8) which are adapted to hold at least one end of a thread loop.

4. The combination of claim 3 wherein the clamping elements (8) include clamping jaws (9) which are spring-loaded in a clamping direction, the clamping jaws (9) being mounted for swivelling movement towards each other and being self-locking counter to a tensioning direction of the thread (2) such that the clamping jaws (9) are adapted to be self-locking when acted upon by thread tension.

5. The combination according to claim 3 wherein the clamping elements (8) include actuating projections (15), the actuating members of the lock assembly holder (5) include actuating elements (7), and the actuating projections (15) are adapted to be acted upon by the actuating elements (7) of the lock assembly holder (5) to move the thread holder (4) to the open position for unclamping the thread.

6. The combination of claim 1 wherein the lock assembly (3) includes a body having a generally central passage (11) defined therethrough which is adapted to receive at least one thread end and for passing a gripping instrument (25) therethrough.

7. The combination of claim 6 wherein the lock assembly holder (5) has a central passage (24) defined therethrough which is in alignment with the central passage of the lock assembly (3) in the coupled position of lock assembly (3) and the lock assembly holder (5), the surgical instrument further comprising forceps (25) which are insertable through said passages.

8. The combination of claim 7 wherein the lock assembly holder (5) has a shaft member (21) which includes inner and outer ends and clasping jaws, the clasping jaws (7) of the lock assembly holder (5) being swivel-mounted at the inner end of the shaft member (21), an inner tube (22) being coaxially located within the shaft member (21) and connected to the clasping jaws (7) for opening and closing the clasping jaws (7), the inner tube (22) having an inner end which is provided with swivel bearings (27) for connection to the clasping jaws (7).

9. The combination of claim 1 wherein the lock assembly holder (5) comprises an actuating and holding element having forcipated clasping jaws (7) which include inner surfaces, the clasping jaws being movable between a first, open position, and a second, closed position, the lock assembly (3) includes actuating projections (15) having an outer contour, the inner surfaces of the clasping jaws (7) being complementary to the outer contour of the lock assembly actuating projections (15) such that the clasping jaws (7) engage the actuating projections (15) in the second, closed position for actuating the thread holder (4) to the open position for unclamping the thread.

10. The combination of claim 9 wherein the lock assembly holder (5) includes a shaft member (21) having inner and outer ends, the clasping jaws (7) of the lock assembly holder (5) are swivel-mounted at the inner end of the shaft member (21), and actuating means for opening and closing the clasping jaws (7) are located at the outer end of the lock assembly holder.

11. The combination of claim 1 wherein the lock assembly (3) has a substantially cylindrical configuration and comprises a lock assembly body having an outer contour and an axial, generally centrally located passage (11) therethrough,
and the thread holder (4) includes clamping elements (8) swivel-mounted on the lock assembly body, the clamping elements (8) include a first end with clamping jaws (9) located in a region of the passage (11) and a second end with actuating projections (15) which extend outside of the outer contour of the lock assembly body.

12. The combination of claim 11 wherein the clamping elements (8) include grooved portions (18) and are spring-loaded into the closed position by at least one rubber ring (10) mounted in the grooved portions (18).

13. The combination of claim 11 wherein the lock assembly (3) has a second passage (19) which extends parallel to the generally centrally located passage (11) and is adapted for securing one end (12) of the thread.

14. The combination of claim 1 wherein the thread holder (4) includes clamping elements (8) which comprise expanding jaws, a generally centrally located passage extends through the lock assembly between the clamping jaws for the thread, an external clamping cone which co-operates with a slidable clamping sleeve being provided on the expanding jaws, the clamping sleeve is spring-loaded in a closing direction of the expanding jaws, and the clamping elements and the clamping cone are provided with contact points for the lock assembly holder for opening and closing the clamping elements.

15. The combination of claim 14 wherein the thread holder (4) includes a second sleeve which is longitudinally slotted in the region of the expanding jaws having a flared outside cross section, and the annular clamping sleeve is slidably mounted upon the second sleeve.

16. The combination of claim 14 wherein one of the expanding jaws and the clamping sleeve have substantially axially extending extensions as contact points for the lock assembly holder, the actuating members are in spaced relationship to one another in the clamping position and include openings therethrough.

* * * * *